(12) United States Patent
Buess et al.

(10) Patent No.: US 10,786,178 B2
(45) Date of Patent: Sep. 29, 2020

(54) BREATHING TUBE FOR USE IN ULTRASONIC FLOW MEASUREMENT SYSTEMS

(71) Applicant: ndd Medizintechnik AG, Zurich (CH)

(72) Inventors: Christian Buess, Horgen (CH); Erich Kleinhappl, Waedenswil (CH); Martin Sengel, Schaffhausen (CH)

(73) Assignee: NDD MEDIZINTECHNIK AG, Zurich (CH)

( * ) Notice: Subject to any disclaimer, the term of this patent is extended or adjusted under 35 U.S.C. 154(b) by 1248 days.

(21) Appl. No.: 14/809,029

(22) Filed: Jul. 24, 2015

(65) Prior Publication Data
US 2016/0128608 A1   May 12, 2016

(30) Foreign Application Priority Data

Nov. 10, 2014   (DE) .................. 10 2014 016 608

(51) Int. Cl.
*A61B 5/087* (2006.01)
*G01F 1/66* (2006.01)
*A61B 5/08* (2006.01)

(52) U.S. Cl.
CPC .............. *A61B 5/087* (2013.01); *A61B 5/082* (2013.01); *G01F 1/662* (2013.01); *A61B 2503/40* (2013.01)

(58) Field of Classification Search
CPC ..... A61B 5/087; A61B 5/082; A61B 2503/40; G01F 1/662; A61M 2205/6063
USPC ......................................... 600/532
See application file for complete search history.

(56) References Cited

U.S. PATENT DOCUMENTS

| | | | |
|---|---|---|---|
| 5,234,117 A | 8/1993 | Garvin | |
| 5,419,326 A * | 5/1995 | Harnoncourt | A61B 5/087 600/438 |
| 5,647,370 A | 7/1997 | Harnoncourt | |
| 5,715,831 A | 2/1998 | Johnson | |
| 5,789,660 A * | 8/1998 | Kofoed | A61B 5/083 422/84 |
| 6,126,610 A * | 10/2000 | Rich | A61M 16/0816 600/529 |
| 6,402,698 B1 * | 6/2002 | Mault | A61B 5/0833 600/531 |

(Continued)

FOREIGN PATENT DOCUMENTS

| | | |
|---|---|---|
| AU | 9170592 B | 7/1991 |
| CN | 101059338 A | 10/2007 |

(Continued)

OTHER PUBLICATIONS

State Intellectual Property Office of the People's Republic of China, Office Action and Search Report Issued in Application No. 201510447957.5, dated Sep. 29, 2018, 14 pages. (Submitted with Partial Translation).

(Continued)

*Primary Examiner* — Victoria Murphy
(74) *Attorney, Agent, or Firm* — McCoy Russell LLP

(57) ABSTRACT

This invention relates to a breathing tube for use in ultrasonic flow measurement systems for determining the volume flow and/or the molar mass of the respiration of humans and animals. According to the invention, the breathing tube at least partly has a polygonal cross-section. Furthermore at least one indicator is formed on the breathing tube, which can be read out via an external optical device.

16 Claims, 5 Drawing Sheets

(56) References Cited

U.S. PATENT DOCUMENTS

Figure 1:
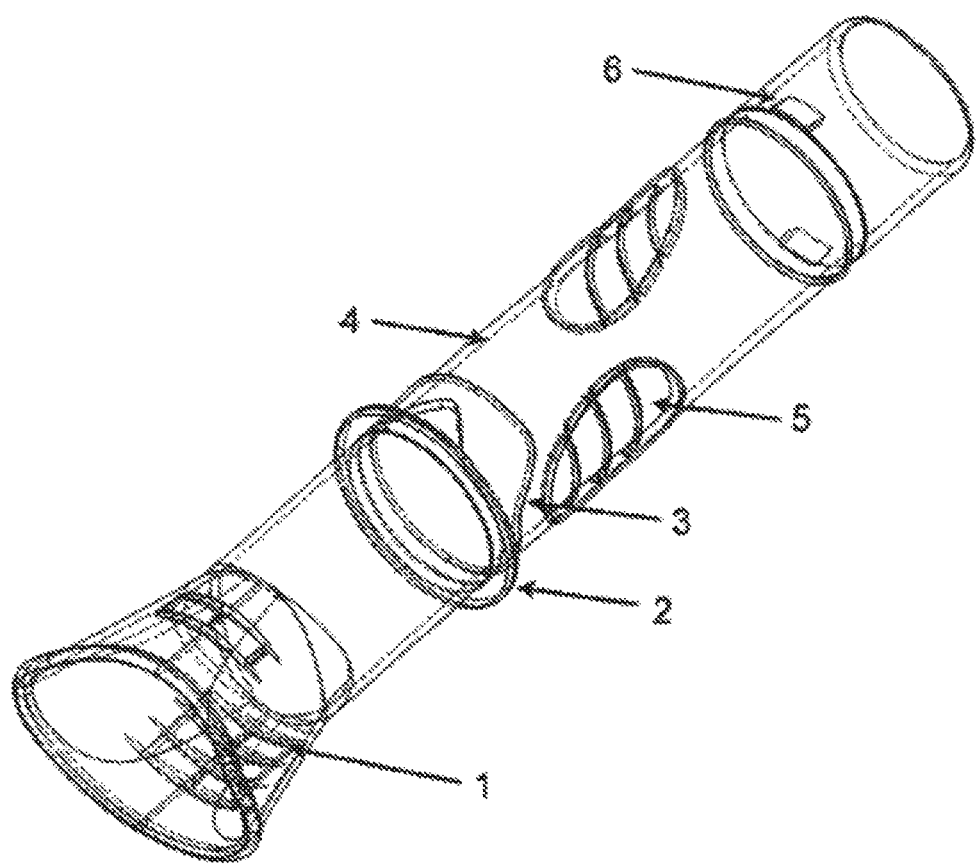

| | | | | |
|---|---|---|---|---|
| 6,427,694 | B1* | 8/2002 | Hecker | A61M 16/06 |
| | | | | 128/201.22 |
| 6,612,306 | B1 | 9/2003 | Mault | |
| 7,018,363 | B2* | 3/2006 | Cowan | A61M 5/1452 |
| | | | | 604/181 |
| 7,635,339 | B2* | 12/2009 | Harnoncourt | A61B 5/087 |
| | | | | 600/529 |
| 2007/0267012 | A1 | 11/2007 | McCarthy | |
| 2007/0283962 | A1* | 12/2007 | Doshi | A62B 23/06 |
| | | | | 128/206.15 |
| 2008/0167568 | A1 | 7/2008 | Rohde et al. | |
| 2008/0283062 | A1* | 11/2008 | Esposito, Jr. | A61B 5/061 |
| | | | | 128/204.23 |

FOREIGN PATENT DOCUMENTS

| | | |
|---|---|---|
| DE | 3941546 A1 | 6/1991 |
| DE | 19605652 A1 | 8/1997 |
| DE | 19910620 A1 | 9/2000 |
| DE | 102007054536 A1 | 7/2008 |
| DE | 102009036288 A1 | 2/2011 |
| EP | 0597060 A1 | 5/1994 |
| EP | 0597060 B1 | 4/1997 |
| EP | 1182431 A1 * 2/2002 ............ G01F 1/662 |  |
| JP | 2002513296 A | 5/2002 |
| JP | 2003511143 A | 3/2003 |
| JP | 2008107234 A | 5/2008 |
| JP | 2013250254 A | 12/2013 |
| KR | 1020030086870 A | 11/2003 |
| WO | 9324810 A1 | 12/1993 |
| WO | 2011015358 A1 | 2/2011 |
| WO | 2014137145 A1 | 9/2014 |

OTHER PUBLICATIONS

Japanese Patent Office, Office Action Issued in Japanese Patent Application No. 2015-040069, dated Mar. 15, 2016, 7 pages.

* cited by examiner

PRIOR ART

BREATHING TUBE FOR USE IN ULTRASONIC FLOW MEASUREMENT SYSTEMS

This invention relates to a breathing tube for use in ultrasonic flow measurement systems for determining the volume flow and/or the molar mass of the respiration of humans and animals.

For measuring the respiratory flow one of the following measurement methods generally is used:
1. Methods which are based on the measurement of the flow-related pressure drop via a resistance in the breathing tube;
2. methods which determine the velocity of the gases by means of cooling of a heated wire in the flow;
3. methods which are based on the measurement of the rotational speed of turbines, and
4. methods which measure the runtimes of ultrasonic pulses running with and against the flow.

In the medical environment, the method based on ultrasonic runtime measurement, which is described in EP 0597060 A1, has been used to an increasing extent for some years. The medical application differs from an industrial application by the following particularities.
There is a very large measurement range with high response speed, i.e. both very high peak flow rates and very low flow rates must be measured exactly with a high sampling rate.
There exist greatly varying gas compositions. In certain medical test methods different gases are used. In the ideal case, the same have no influence on the measurement of the respiratory flow velocity.
Good hygienic properties must exist. This means that the device must be suitable for cleaning during a change of patients, in order to avoid a cross-contamination under all circumstances.

In flow measurement devices which are based on ultrasonic runtime measurement, replaceable breathing tubes frequently are used to avoid cross-contamination. In EP 0597060 B1, U.S. Pat. No 5,419,326 and U.S. Pat. No. 5,647,370 such replaceable breathing tubes are described.

The breathing tubes used so far substantially have a round or slightly oval cross-section. Often, an inside diameter of 20 mm is preferred, because the same corresponds to a tube diameter widely used in anesthesia. FIG. 1 shows an exemplary embodiment of a breathing tube according to this prior art for use in spirometers for lung function diagnostics. The breathing tube includes the following elements:
an integrated mouthpiece 1 which the patient encloses with the lips,
a ring 2 with triangular position mark which clearly defines the position of the breathing tube in the measurement system,
sealing lips 3 which seal the breathing tube against the measurement system,
a body 4 of the breathing tube with a circular inside diameter of about 20 mm,
oval sound openings 5 which allow an ultrasound transmission between the two obliquely arranged transmitting and receiving elements of the ultrasonic flow measurement system no longer shown here, and
a barb 6 which prevents that the breathing tube can inadvertently be pushed out again from the measurement system.

The breathing tubes usually are manufactured in injection molding technique. The openings of the sound openings usually are provided with nets which during the production process are injection-molded into the material. These nets have a very small open surface, allow a transmission of sound pulses, and on the other hand prevent a stall and thus strong turbulences in the breathing tube. As only one breathing tube is used per patient, these nets prevent that a cross-contamination can occur between patients.

Due to their construction, however, the above-described replaceable breathing tubes have some disadvantages which are listed below:
The ring with the triangular position mark does not guarantee that the breathing tube always is pushed into the measurement system by the user in exactly the same position.
The breathing tube for example cannot be pushed in completely or not be aligned exactly either (undesired rotation of the breathing tube). A breathing tube which is not positioned correctly in the measurement system however leads to measurement errors in the speed measurement.
The ultrasonic penetration of the measurement path is not optimal in a round cross-section and does not cover the upper or lower parts of the air stream. An unequal distribution of the air stream over the cross-section also can lead to measurement errors.

It is the object of the invention to develop a generic breathing tube such that the aforementioned disadvantages are eliminated. In particular, it should be detected in the system whether a breathing tube is inserted in its correct position.

According to the invention, this object is solved by the combination of the features of claim 1. In the generic breathing tube for use in ultrasonic flow measurement systems for determining the volume flow and/or the molar mass of the respiration of humans and animals the breathing tube accordingly is at least partly designed with a polygonal cross-section. The breathing tube includes at least one indicator which can be read out via an external optical device.

The at least partly provided polygonal cross-section of the breathing tube prevents that the breathing tube can be inserted into the measurement system in a twisted way. Preferably, the polygonal cross-section for this purpose is designed asymmetric, in order to prevent a wrong insertion of the breathing tube (for example by inadvertently twisting by a certain angular amount).

Via the at least one indicator, the presence of the breathing tube in the measurement system can be detected automatically. In addition, the correct positioning on the longitudinal axis of the breathing tube within the measurement system also can be ensured. Via the selection of the indicator, an information on the type of the breathing tube can be read out in addition.

Advantageous aspects of the invention can be taken from the sUb-claims following the main claim.

Accordingly, the at least one indicator can be formed by areas on the outer surface of the breathing tube, which differ from the remaining surface of the breathing tube by the color and/or the degree of reflection. Due to this formation of the at least one indicator, the same can be read out via an optical device, such as for example a light barrier or a reflection light barrier. These light barriers are integrated in the corresponding ultrasonic flow measurement system in which the breathing tube is used.

According to a particularly advantageous aspect of the invention, the at least one indicator can be formed by the shape of the outer surface of the breathing tube. For forming the at least one indicator, the breathing tube for example can be formed comb-like in the region of at least one edge. Through the spaces in the comb-like edge surface formed thereby light beams for example can pass to impinge onto the optical sensors.

According to a further advantageous aspect of the invention, the breathing tube has an almost rectangular cross-section, wherein the outsides of the breathing tube extend slightly beveled. It can herewith be prevented that the breathing tube inadvertently is inserted into the measurement system offset by 180°.

Advantageously, the breathing tube has at least one circumferential sealing lip on its surface. The at least one sealing lip in cooperation with the measurement device into which the breathing tube can be inserted, can effect a secure sealing with the inner surface of the measurement device, i.e. of the ultrasonic flow measurement system, due to a resulting uniform force acting to the outside.

The openings in the breathing tube, which serve for passing through the ultrasonic pulses, advantageously are closed via a fabric-like net. The fabric-like net can each be injectable from the same material during the injection-molding operation for producing the breathing tube made of an injectable plastic material. Alternatively, however, the fabric-like net also can be made of a material different from the breathing tube and be connectable with the breathing tube in a separate working step for covering the opening.

According to another advantageous aspect of the invention, the breathing tube can include a mouthpiece to be plugged on separately.

Furthermore, the breathing tube additionally can include a filter which preferably also can be designed to be plugged on.

Finally, the breathing tube also can have at least one protrusion on its outer surface, via which the breathing tube can be pushed out of the ultrasonic flow measurement system.

Advantageously, different types of the breathing tube can have different inner cross-sections, so as to be optimized for special applications with respect to the volume of the breathing tube and the measurement resolution.

A reliable detection of the type of the breathing tube via the at least one indicator additionally advantageously provides for an adaptation of the measurement evaluation of the ultrasonic flow measurement system. The linearization of the measured flow signal, i.e. of the mathematical connection between the measured transit times and the output speed of the volume flow, can be adjusted to the respectively used breathing tube.

Figure 2:
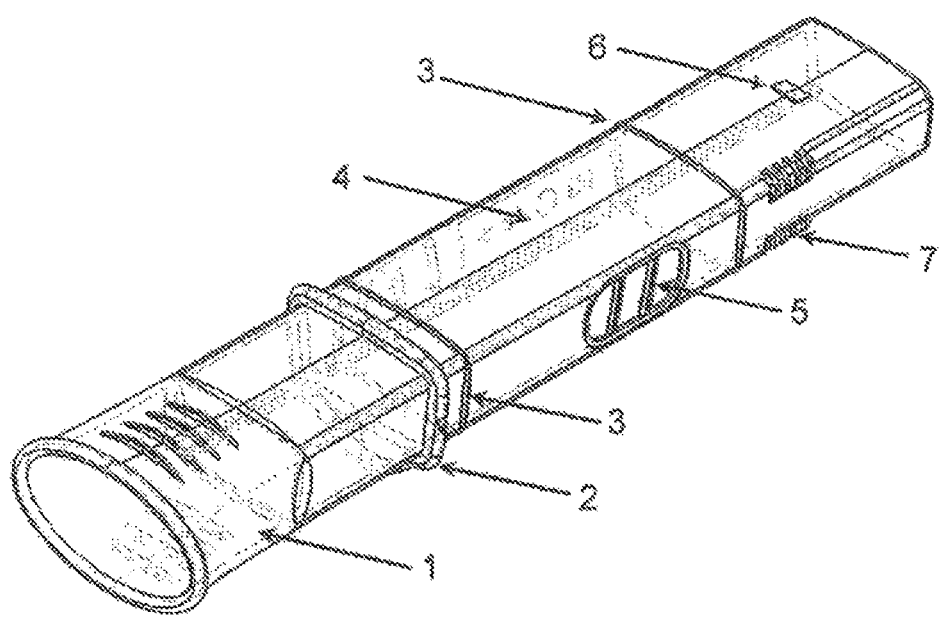
Figure 3:
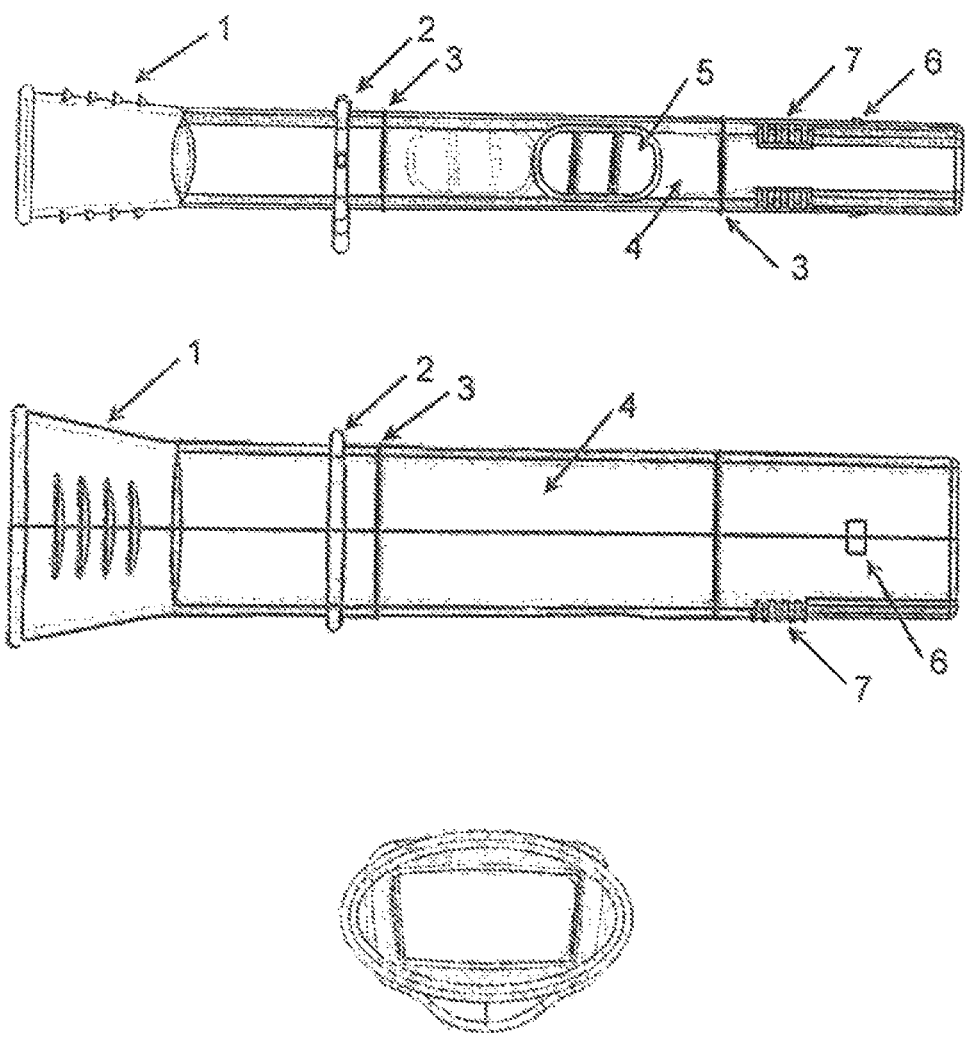
Figure 4:
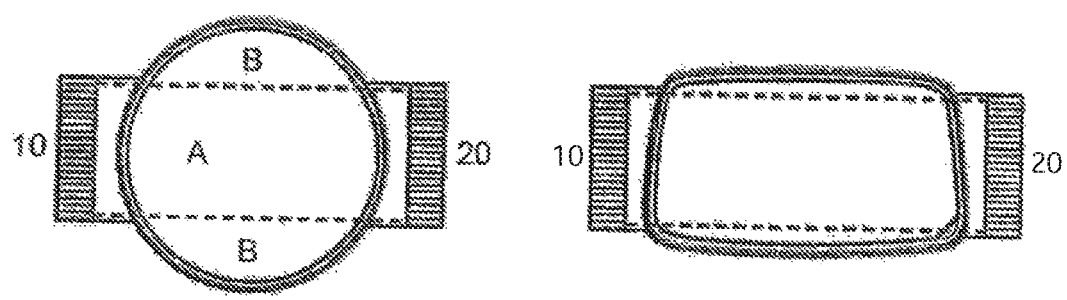
Figure 5:
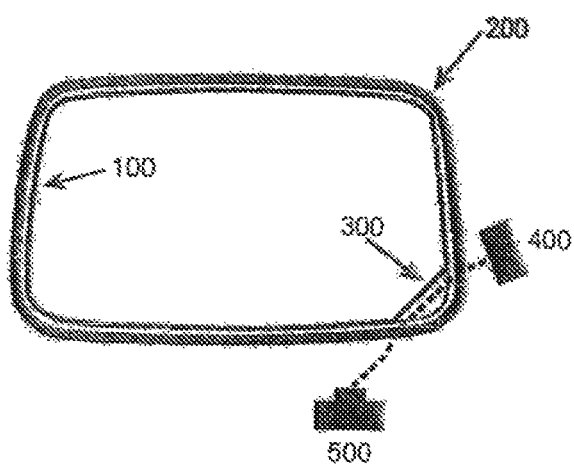
Figure 6:
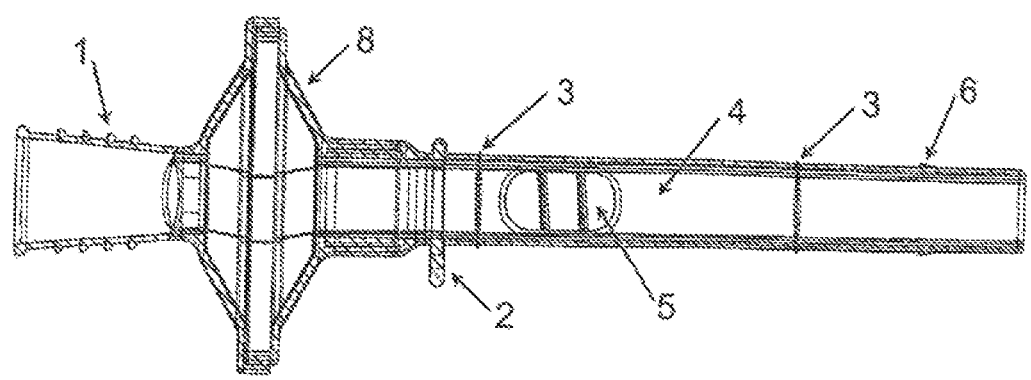

Further features, details and advantages of the invention will be explained in detail with reference to exemplary embodiments shown in the drawing, in which:

FIG. 1: shows a schematic representation of a breathing tube according to the prior art;

FIG. 2: shows a perspective view of a first embodiment of the breathing tube according to the invention;

FIG. 3: shows the breathing tube according to FIG. 2 in side, top and front views;

FIG. 4: shows a schematic representation to illustrate the penetration of the measurement path for a round and a rectangular breathing tube;

FIG. 5: shows a cross-section through the breathing tube according to FIG. 2; and FIG. 6: shows a longitudinal section through a breathing tube according to a second embodiment of the invention.

An embodiment of the breathing tube according to the invention is shown in FIG. 2 in a perspective view. This breathing tube serves for insertion into a non-illustrated ultrasonic flow measurement device, as it is known for example from EP 0597060 A1. This breathing tube is designed for single use in a patient and is provided with mechanical indicators which can be detected via an optical system. In the perspective view according to FIG. 2 it can be seen that the breathing tube includes an integrated mouthpiece 1. A corresponding stop ring 2 with ejection tab defines the end position on insertion into the non-illustrated measurement system and on the other hand by means of the ejection tab provides for easily pushing out the breathing tube after its use.

The breathing tube has two circumferential sealing lips 3 in its front and rear regions, which serve for sealing against the ultrasonic measurement system not shown here. The actual body 4 of the breathing tube has an approximately rectangular cross-section, wherein the side walls however are slightly beveled. Strictly speaking, this results in a trapezoidal shape with rounded corners. The two provided openings on the opposite sides of the breathing tube, which serve for the transmission of ultrasound, each are closed with nets. Finally, a barb 6 is injection-molded to the breathing tube, which prevents that the breathing tube can inadvertently be pushed out again from the measurement system.

In the upper and lower edge regions of the breathing tube two mechanical indicators in the form of an injection-molded comb-like structure each are provided in the edge on the outer surface. FIG. 3 shows the above-described realization variant in addition in side, top and front views. The front view illustrates the substantially rectangular cross-section of the breathing tube. It can likewise be seen that due to their bevel the side walls are designed such that the breathing tube cannot be inserted into the measurement system when it is rotated by 180°.

As compared to the previously used breathing tubes for use in ultrasonic flow measurement systems, the breathing tube of the present invention has an almost rectangular cross-section in the exemplary embodiment shown here. As compared to a round or slightly oval cross-sectional shape, this shape has a better "penetration" of the cross-section by the ultrasound beam.

FIG. 4 shows two variants of a breathing tube together with the laterally arranged ultrasonic cells. The ultrasonic cells are designated with 10 and 20, respectively. The same are both transmitter and receiver of ultrasonic signals. The area between the two interrupted lines A between the ultrasonic cells represents the region of the volume flow covered by the ultrasound beam. This means that in this region the volume flow in the breathing tube can be measured by the ultrasound beam. The entire volume flow in the outer region B, on the other hand, is not detected by the ultrasound. With a non-uniform distribution of the volume flow over the cross-section of the breathing tube, this effect leads to errors in the measurement result. In the case of the rectangular cross-section of the breathing tube, the ratio of the areas A to B is better, i.e. a larger percentage of the volume flow actually is detected by the ultrasonic measurement signal. In the right embodiment in FIG. 4, which substantially corresponds to the shape of the present configuration of the invention, this hence will lead to a reduction of the error in the case of a non-uniform distribution of the volume flow in the breathing tube.

FIG. 5 shows a realization variant of the optical detection of the mechanical indicators of the breathing tube 100, which is inserted in an ultrasonic flow measurement system, which here is designated with 200. In the representation, the breathing tube includes a comb-like structure 300 which is aligned in longitudinal direction, in the bottom right region of the breathing tube. The comb-like structure already is shown in principle in FIG. 2 in the perspective representation. Via a light source 400, for example an LED source, a light beam is passed over the comb-like indicator to the line sensor 5. The breathing tube holder of the measurement system 200 for this purpose must be transparent in the region of the indicator. The light source and the associated beam path must be designed such that the comb-like structure is depicted completely on the line sensor. By reading out the information of the line sensor, different items of information can be obtained and be processed in the system:

a) the presence of a breathing tube, b) the positions of the breathing tube within the measurement system, and c) the type of the breathing tube.

The position of the breathing tube can be detected, since the indicators are arranged along the longitudinal axis. For detecting the type of breathing tube, the same is encoded in the structure of the comb-like indicator. Elevations and depressions in the mechanical structure of the indicator produce characteristic sequences of light and shadow on the line sensor. From this image of the indicator on the line sensor, an identification number can be calculated in the controller of the ultrasonic flow measurement system. The controller may include instructions stored in memory of the controller and including instructions to carry out the actions described herein, including to calculate the identification number, and further transmit and/or display the identification number, and/or adjust operating parameters of the flow measurement system and/or another device in response to the calculated identification number.

FIG. 6 shows a longitudinal section through an alternative design variant of the breathing tube according to the invention. In principle, this breathing tube corresponds to the one of FIG. 2. In contrast to the design variant shown in FIG. 2, however, the mouthpiece 1 and an additional filter insert 8 here are connected with the residual body 4 of the breathing tube in a manner to be plugged on. The plug-in connection provided here allows an easy replacement of mouthpiece 1 and/or filter insert 8.

In one embodiment, an ultrasonic flow measurement system may comprise a breathing tube for use in for determining the volume flow and/or the molar mass of the respiration of humans and animals, wherein the breathing tube at least partly has a polygonal cross-section and on the breathing tube at least one indicator is formed, which is readable out via an external optical device into the flow measurement system for further processing and/or display by the flow measurement system.

The invention claimed is:

1. A breathing tube for use in an ultrasonic flow measurement system for determining a volume flow and/or a molar mass of respiration of humans and animals, wherein the breathing tube at least partly has a polygonal transversal cross-section extending along a longitudinal axis of the breathing tube, and the breathing tube has at least a pair of beveled outer sides opposing one another and extending along the longitudinal axis that permit insertion of the breathing tube into the measurement system when the breathing tube is in a predetermined orientation in relation to the measurement system and that prevent insertion of the breathing tube into the measurement system if the breathing tube is rotated 180 degrees about the longitudinal axis relative to the predetermined orientation, and wherein on the breathing tube at least one indicator is formed, which is readable out via an external optical device, wherein an outer surface of the breathing tube comprises a comb-like shape to form the at least one indicator in a region of at least one edge of the breathing tube, wherein openings in the breathing tube, which serve for passing through ultrasonic pulses, are arranged on the pair of beveled outer sides.

2. The breathing tube according to claim 1, wherein the at least one indicator is formed by areas on the outer surface of the breathing tube that differ from a remainder of the outer surface by a color and/or a degree of reflection.

3. The breathing tube according to claim 1, wherein the polygonal transversal cross-section comprises a substantially trapezoidal interior cross-section.

4. The breathing tube according to claim 1, wherein the polygonal transversal cross-section comprises a substantially trapezoidal cross-section.

5. The breathing tube according to claim 4, wherein the breathing tube has at least one circumferential sealing lip on the outer surface of the breathing tube.

6. The breathing tube according to claim 5, wherein the outer surface of the breathing tube has a curved shape such that in cooperation with the measurement system, into which the breathing tube is insertable, the at least one circumferential sealing lip effects secure sealing due to a resulting uniform force acting onto an outside of the at least one sealing lip.

7. The breathing tube according to claim 6, wherein the openings in the breathing tube are closed via a fabric-like net.

8. The breathing tube according to claim 7, wherein the fabric-like net is made from a same injectable plastic material as the breathing tube as to be injectable from the same injectable plastic material during an injection-molding operation for producing the breathing tube.

9. The breathing tube according to claim 7, wherein the fabric-like net is made of a material different from the breathing tube.

10. The breathing tube according to claim 9, wherein the breathing tube includes a mouthpiece to be plugged on separately.

11. The breathing tube according to claim 10, wherein the breathing tube has at least one protrusion on the outer surface via which the breathing tube can be pushed out of the measurement system.

12. The breathing tube according to claim 1, wherein the breathing tube has at least one circumferential sealing lip on the outer surface of the breathing tube.

13. The breathing tube according to claim 1, wherein the openings in the breathing tube are closed via a fabric-like net.

14. The breathing tube according to claim 1, wherein the breathing tube includes a mouthpiece to be plugged on separately.

15. The breathing tube according to claim 1, wherein the breathing tube includes a filter which is plugged on.

16. The breathing tube according to claim 1, wherein the breathing tube has at least one protrusion on the outer surface via which the breathing tube can be pushed out of the measurement system.

* * * * *